US00PP17986P3

(12) United States Plant Patent
Jennings

(10) Patent No.: US PP17,986 P3
(45) Date of Patent: Sep. 4, 2007

(54) RASPBERRY PLANT NAMED 'JOAN IRENE'

(50) Latin Name: *Rubus idaeus*
Varietal Denomination: Joan Irene

(75) Inventor: Derek L. Jennings, Maidstone (GB)

(73) Assignee: Medway Fruits, Maidstone, Kent (GB)

( * ) Notice: Subject to any disclaimer, the term of this patent is extended or adjusted under 35 U.S.C. 154(b) by 61 days.

(21) Appl. No.: 11/181,982

(22) Filed: Jul. 15, 2005

(65) Prior Publication Data

US 2007/0016987 P1 Jan. 18, 2007

(51) Int. Cl.
*A01H 5/00* (2006.01)

(52) U.S. Cl. ..... Plt./204

(58) Field of Classification Search ..... Plt./204
See application file for complete search history.

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct *Rubus idaeus* L. plant is provided that is the product of a controlled breeding program. The new Raspberry plant abundantly forms attractive conical-shaped Cardinal Red fruit which commonly is lighter in coloration than that of the 'Joan J' cultivar (non-patented in the United States). The fruit commonly starts to ripen approximately four weeks later than that of the 'Joan J' cultivar in Southern England. Also, the mature fruit is firmer than that of the 'Joan J' cultivar, and is well suited for consumption as high grade fresh fruit.

1 Drawing Sheet

Figure 1:
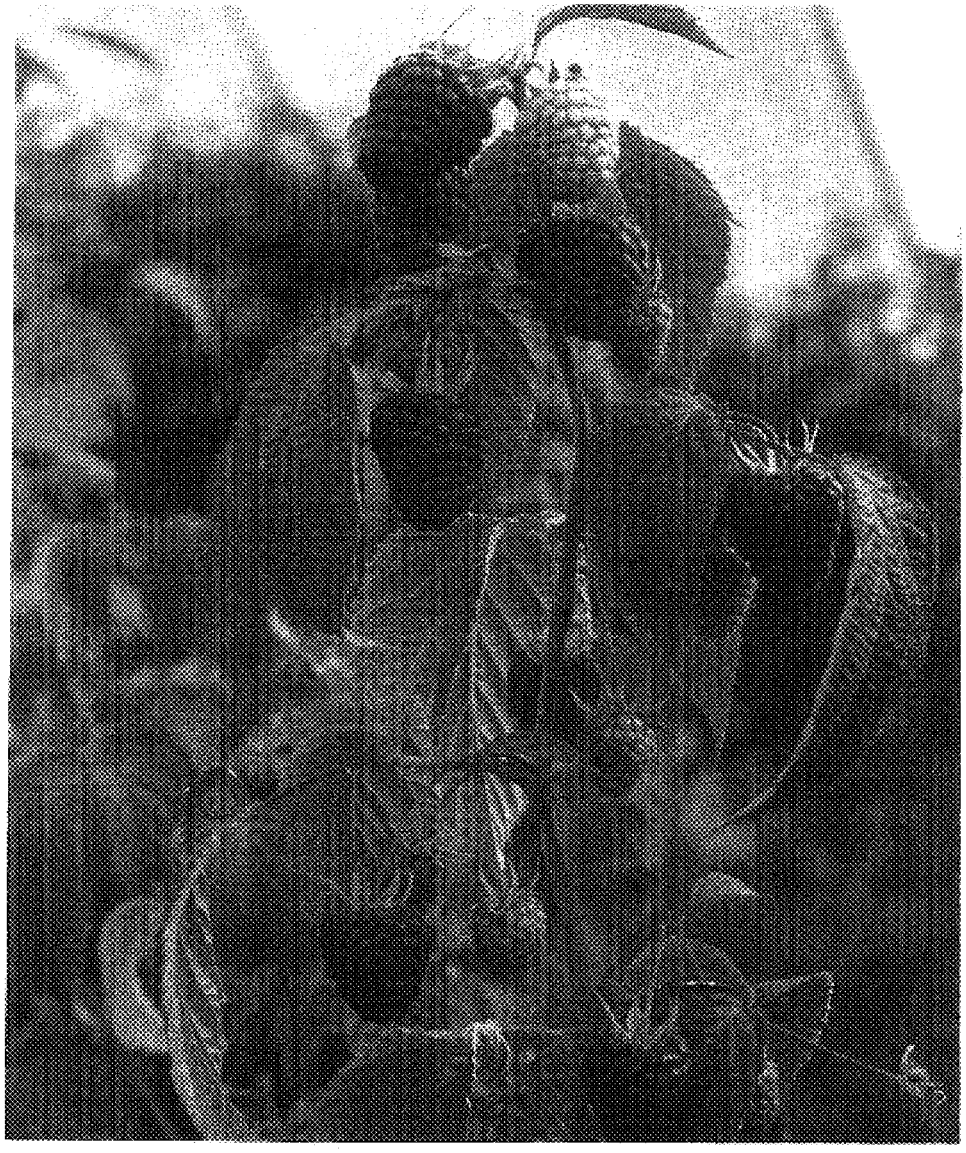

Botanical/commercial classification: *Rubus idaeus*/Raspberry Plant.
Varietal denomination: cv. Joan Irene.

SUMMARY OF THE INVENTION

The instant plant (i.e., *Rubus idaeus* L.) was created in the course of a planned breeding program carried out at Maidstone, Kent, United Kingdom. Two parents were crossed in the hope that they would contribute the desired characteristics. The female parent (i.e., the seed parent) was the 'Joan J' cultivar (non-patented in the United States). Such 'Joan J' cultivar is recognized to be a high-yielding early primocane-fruiting cultivar that is a cross between the 'Joan Squire' and 'Terri-Louise' cultivars (both non-patented in the United States). The male parent (i.e., the pollen parent) was an unreleased *Rubus idaeus* plant from the breeding program designated '93122/1' (non-patented in the United States). No plants of '93122/1' presently exist. The parentage of the new cultivar can be summarized as follows:

'Joan J'×'93122/1'.

The seeds resulting from the above pollination were sown and small plants were obtained which were physically and biologically different from each other. Selective study resulted in the identification of a single plant of the new cultivar.

It was found that the new Raspberry plant of the present invention possesses the following combination of characteristics:

(a) abundantly forms attractive conical-shaped Cardinal Red fruit which commonly is lighter in coloration than that of the 'Joan J' cultivar when mature, (b) commonly produces fruit that starts to ripen approximately four weeks later than the 'Joan J' cultivar in Southern England, and (c) produces mature fruit that is firmer than that of the 'Joan J' cultivar and is well suited for consumption as high grade fresh fruit.

The new cultivar well meets the needs of the berry industry. The firmer nature of the mature fruit is advantageous during picking, shipment, and marketing.

The new cultivar can be readily distinguished from its 'Joan J' parent in view of its ripening time, fruit coloration, and firmness.

The new cultivar has been found to undergo asexual propagation at Maidstone, Kent, United Kingdom by in vitro tissue culture and by the rooting of cuttings. Asexual propagation by the above-mentioned methods as performed at such location has shown that the characteristics of the new cultivar are strictly transmissible from one generation to another. Accordingly, the new variety undergoes asexual propagation in a true-to-type manner.

The new cultivar initially was designated 96303/11, and subsequently has been named 'Joan Irene'.

BRIEF DESCRIPTION OF THE PHOTOGRAPH

The accompanying photograph shows as nearly true as is reasonably possible to make the same in a color illustration of this character a typical specimen of the new cultivar. The photograph was obtained on Aug. 11, 2002 at Maidstone, Kent, United Kingdom. The illustrated plant had been planted during the Spring of 2001.

FIG. 1 illustrates a fruiting plant where the foliage and fruit in various stages of development are illustrated. The attractive Cardinal Red conical-shaped mature fruit of the new cultivar is shown.

DETAILED DESCRIPTION

The chart used in the identification of color is that of The Royal Horticultural Society (R.H.S. Colour Chart). The description is based on the observation of specimens of the new cultivar growing at Maidstone, Kent, United Kingdom.

Botanical classification: *Rubus idaeus* L.

Plant: The new cultivar is being grown for its primocane fruit crop. The primocanes commonly are Green Group 142C in coloration. Forms a medium number of current season shoots. The very young shoots commonly lack anthocyanin coloration at the apex. Spines are absent on the stems and canes.

Foliage: The leaflets commonly number three or five. Typical terminal leaflets from among three leaflets commonly are approximately 12.5 cm in length and approximately 11.4 cm in width. Typical terminal leaflets from among five leaflets commonly are approximately 13.0 cm in length and approximately 8.3 cm in width. The leaflets commonly are Green Group 137C on the upper surface and Green Group 138B on the under surface. The leaflets commonly possess a cuspidate apex and a cordate base. The petioles commonly are smooth Yellow-Green Group 145A in coloration, and commonly measure approximately 5.8 cm in length to mature leaves.

Flowering: Commonly the second week of July to the first week of August at Maidstone, Kent, United Kingdom. The flowers are pure white, White Group 155D. The peduncles commonly are smooth, Yellow-Green Group 145A in coloration, and approximately 4.5 cm in length.

Time of fruiting: Late, during August and commonly late August at Maidstone, Kent, United Kingdom. The time when ripening begins commonly is approximately four weeks later than that of the 'Joan J' cultivar at such location. The time of when fruit begins to ripen is similar to that of the 'Korbfüller' cultivar (non-patented in the United States).

Bearing type: Fruit mainly is borne on the current season's canes similar to that of the 'Autumn Bliss' cultivar (U.S. Plant Pat. No. 6,597).

Fruit character: Generally conical-shaped and similar to that of the 'Annamaria' cultivar (U.S. Plant Pat. No. 11,102) and the 'Rafzmach' cultivar (non-patented in the United States). The coloration of the mature fruit is Cardinal Red, Red Group 53C, and commonly is lighter than that of its 'Joan J' ancestor. The mature fruit commonly also is firmer than that of its 'Joan J' ancestor. Such firmness is beneficial when picking, handling, and when transporting to the marketplace. The typical fruit weight common is approximately 4.75 grams, the typical fruit length commonly is approximately 3.0 cm, and the typical fruit diameter commonly is approximately 2.5 cm. Since the new cultivar is being grown for its primocane fruit crop, the fruiting propensity on floricanes has not been evaluated. However, the size of the fruit produced on the floricanes is believed to be approximately one-third smaller than that produced on primocanes. The typical primocane crop at Maidstone, Kent, United Kingdom, one year after planting has been observed to be approximately 9t/ha.

Resistance to pests and diseases: During observations to date the new cultivar of the present invention has displayed adequate resistance to all pests and diseases encountered at Maidstone, Kent, United Kingdom.

Virus status: Plant material of the new cultivar has been tested against all viruses indicated by graft testing to *Rubus occidentalis*. Also, sap inoculations to *Chenopodium guinea,* and ELIZA testing to Raspberry Bushy Dwarf virus has been carried out.

Market: The berries are suitable for consumption as high grade fresh fruit and also are amenable to processing.

I claim:

1. A new and distinct cultivar of Raspberry plant having the following combination of characteristics:

(a) abundantly forms attractive conical-shaped Cardinal Red fruit which commonly is lighter in coloration than that of the 'Joan J' cultivar when mature, (b) commonly produces fruit that starts to ripen approximately four weeks later than the 'Joan J' cultivar in Southern England, and (c) produces mature fruit that is firmer than that of the 'Joan J' cultivar and is well suited for consumption as high grade fresh fruit;

substantially as illustrated and described.

* * * * *